(12) United States Patent
Haduong

(10) Patent No.: US 8,225,797 B2
(45) Date of Patent: *Jul. 24, 2012

(54) METHOD AND SYSTEM FOR SWALLOW CONTROL RESULTING IN IMPROVED POSTURE AND STRENGTH

(76) Inventor: Han Haduong, Downey, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/886,303

(22) Filed: Sep. 20, 2010

(65) Prior Publication Data

US 2011/0226259 A1 Sep. 22, 2011

Related U.S. Application Data

(62) Division of application No. 11/699,694, filed on Jan. 30, 2007, now Pat. No. 7,798,149.

(51) Int. Cl.
*A61G 15/00* (2006.01)
*A61F 5/56* (2006.01)
*A61C 5/14* (2006.01)
*A61C 3/00* (2006.01)

(52) U.S. Cl. ........ 128/845; 128/848; 128/859; 128/861; 433/6

(58) Field of Classification Search ................ 128/848, 128/859–862, 140; 433/6–7
See application file for complete search history.

(56) References Cited

U.S. PATENT DOCUMENTS

| | | | | |
|---|---|---|---|---|
| 2,678,043 A | 5/1954 | Stark | | 128/136 |
| 2,966,908 A | 1/1961 | Cathcart et al. | | 128/136 |
| 3,124,129 A | 3/1964 | Grossberg | | 128/136 |
| 3,478,429 A | 11/1969 | Shilliday | | 32/14 |
| 3,871,370 A | * | 3/1975 | McDonald | 128/860 |
| 4,608,974 A | | 9/1986 | Sicurelli, Jr. | 128/136 |
| 4,668,188 A | * | 5/1987 | Wolfenson et al. | 433/37 |
| 4,718,662 A | * | 1/1988 | North | 482/11 |
| 4,997,182 A | * | 3/1991 | Kussick | 482/11 |
| 5,052,409 A | | 10/1991 | Tepper | 128/859 |
| 5,152,301 A | * | 10/1992 | Kittelsen et al. | 128/861 |
| 5,169,316 A | | 12/1992 | Lorman et al. | 434/185 |
| 5,213,553 A | | 5/1993 | Light | 482/11 |
| 5,259,762 A | | 11/1993 | Farrell | 433/215 |
| H1557 H | | 7/1996 | Joubert et al. | 128/782 |

(Continued)

FOREIGN PATENT DOCUMENTS

WO WO 95/14449 6/1995

*Primary Examiner* — Patricia Bianco
*Assistant Examiner* — Ophelia Hawthorne
(74) *Attorney, Agent, or Firm* — Clifford Kraft

(57) ABSTRACT

A method and system for training a patient to improve swallowing, for retraining jaw muscles and for holding or keeping the jaw in a correct bite position. All of this in-turn causing an improvement in posture and increase strength. The system includes a combination of exercise and oral apparatus pieces or mouth-guards to retrain and balance the facial muscles and to develop a correct swallow. The mouth-guards of the present invention can improve biomechanical imbalance, posture and in turn athletic performance. A particular embodiment of an oral apparatus of the present invention includes top and bottom troughs for receiving top and bottom teeth into the apparatus. The troughs can be adapted to hold the upper canine teeth lower than the central and lateral incisor teeth and hold the upper teeth outside the lower teeth from the incisors to the molars. The apparatus can be pre-fabricated or custom made for a particular patient. Using heat moldable thermoplastics, some embodiments of the device can be formed in the patient's mouth after heating in hot water.

1 Claim, 11 Drawing Sheets

U.S. PATENT DOCUMENTS

| | | | |
|---|---|---|---|
| 5,592,951 A * | 1/1997 | Castagnaro et al. | 128/848 |
| 5,624,257 A * | 4/1997 | Farrell | 433/6 |
| 6,082,363 A * | 7/2000 | Washburn | 128/859 |
| 6,505,625 B1 * | 1/2003 | Uenishi | 128/848 |
| 6,971,993 B2 | 12/2005 | Fletcher | 600/587 |
| 7,059,332 B2 * | 6/2006 | Eli | 128/898 |
| 2005/0045190 A1 * | 3/2005 | Bennett | 128/898 |

* cited by examiner

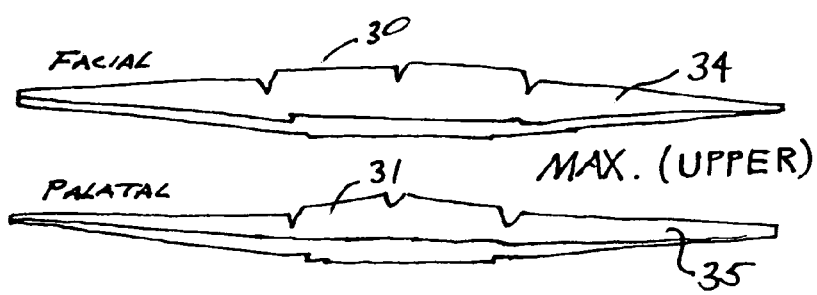
FIG. 2A
FIG. 2B
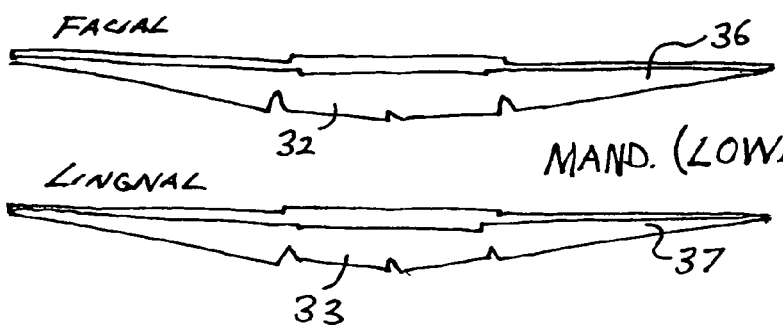
FIG. 2C
FIG. 2D

METHOD AND SYSTEM FOR SWALLOW CONTROL RESULTING IN IMPROVED POSTURE AND STRENGTH

This is a continuation-in-part of application Ser. No. 11/699,694 filed Jan. 30, 2007. Application Ser. No. 11/699,694 is hereby incorporated by reference.

BACKGROUND

1. Field of the Invention

The present invention relates generally to the field of relating swallowing to posture and more particularly to a method and system for swallow control that results in an improved posture, improved upper and lower jaw position, increased strength and widening of the upper jaw's bones and teeth.

2. Description of the Prior Art

It is known in the art that posture is affected by breathing, visual control and body mobility. It is less known that posture is also affected by swallowing. A poor relationship between the lower jaw position and the upper jaw can lead to a biomechanical imbalanced posture. The upper and lower jaw affects throat volume, the swallow and in turn the posture and strength; this in turn can affect athletic performance.

It is also known in the art to use various mechanical appliances in the mouth to change the relationship of the jaws, straighten teeth and strengthen muscles. U.S. Pat. No. 3,478,429 teaches an orthodontic tooth-positioner and retaining device for example. It is also known to use mechanical appliances in the mouth to provide protection in contact sports. U.S. Pat. No. 2,966,908 teaches such a mouth protector. Another example is taught in U.S. Pat. Nos. 2,678,043 and 3,124,129. U.S. Pat. Nos. 2,678,043, 2,966,908, 3,478,429 and 3,124,129 are hereby incorporated by reference.

There are several deformities of the jaw that are due to imbalanced facial muscles. For example, a retrude jaw or deep bite as well as a gummy smile where the upper jaw is tipped down and more forward than the lower jaw are both caused by muscle imbalance.

The prior art generally does not teach a combination of mouth or swallowing exercise and an appliance or group of appliances to improve both the shape of the mouth and the posture. What is badly needed is a method that teaches various exercises coupled with appliances to improve upper and lower jaw positioning, size and shape, strength and to improve posture. It would also be advantageous to have an appliance that could be used to continue the treatment or exercise by wearing it at night while a patient sleeps.

Most available mouth-guards do not take into account that the lower jaw position will affect posture and athletic performance. It would be advantageous to have a mouth guard using a special approach to set the lower jaw at the swallow bite such that the body does not need to compensate for the jaw during swallowing. A mouth guard that sets the jaw at the ideal position for swallowing would improve the biomechanical balanced, posture and in turn improve athletic performance.

SUMMARY OF THE INVENTION

The present invention relates to a method and system for training a patient to improve swallowing, for retraining jaw muscles and for holding or keeping the jaw in a correct bite position. All of this in-turn causing an improvement in posture. The system includes a combination of exercise and oral apparatus pieces and/or mouth-guards to retrain and balance the facial muscles and to develop a correct swallow. The mouth-guards of the present invention can improve biomechanical imbalance, posture and in turn athletic performance.

A particular embodiment of an oral apparatus of the present invention includes top and bottom troughs for receiving top and bottom teeth into the apparatus. The troughs can be adapted to hold the upper canine teeth lower than the central and lateral incisor teeth and hold the upper teeth outside the lower teeth from the incisors to the molars. The apparatus can be pre-fabricated or custom made for a particular patient. Using heat moldable thermoplastics, some embodiments of the device can be formed in the patient's mouth after heating in hot water.

DESCRIPTION OF THE FIGURES

Attention is directed to the following figures that better illustrate some of the concepts of the present invention.

FIGS. 2A-2D show more views of the embodiment of FIG. 1.

Figure 1A:
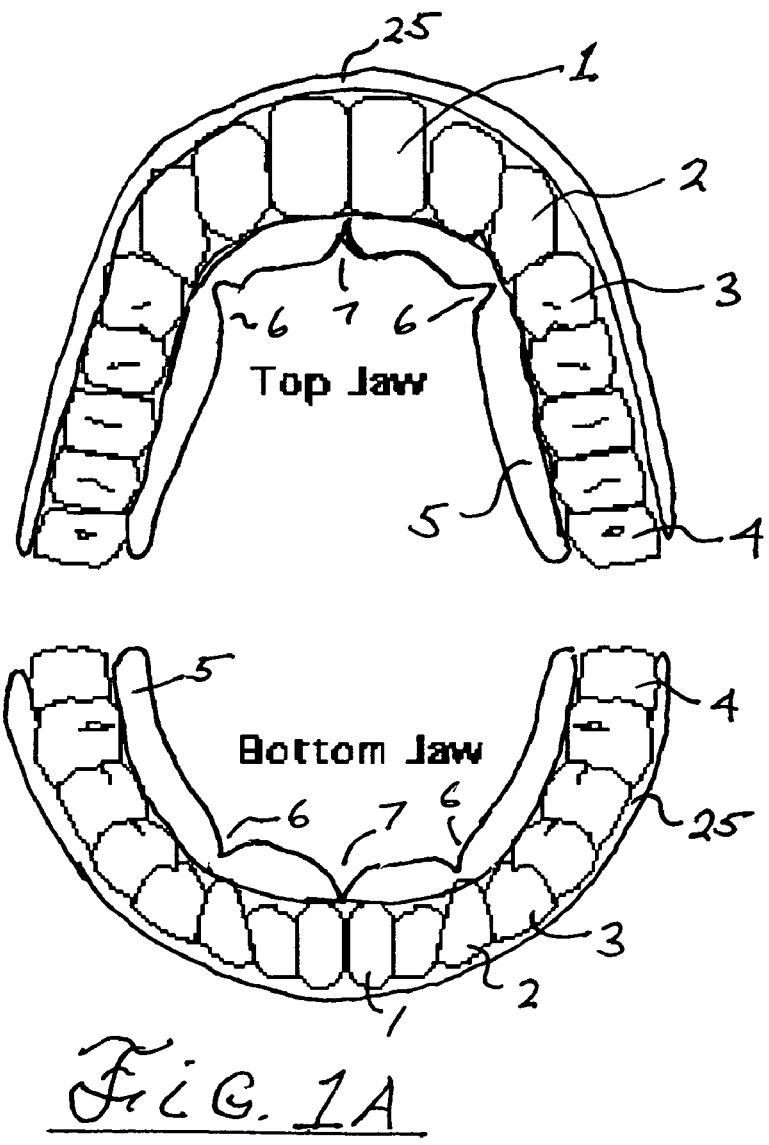
FIGS. 1A-1G show a prefabricated full-mouth appliance used to aid in a jaw muscle exercise.

Several drawings and illustrations have been presented to better aid in the general understanding of the invention. The scope of the present invention is not limited to what is shown in the figures.

DESCRIPTION OF THE INVENTION

The present invention relates to a method and system for training a patient to improve swallow, for retraining jaw muscles and for holding or keeping the jaw in a correct bite position. All of this in-turn causes an improvement in posture which is improved because, with proper swallow, the throat volume is increased and the oral facial muscles are more balanced.

When a human swallows, the tongue performs a peristaltic motion pushing food rearwards and finally down into esophagus and the stomach. The oral cavity behind the teeth is mostly occupied by the tongue. The tongue has the ability to rise up and down and create a wave that propels food backward. The swallowing process starts when a food is loaded onto the tongue. The posterior oral cavity is closed at this point at the glossopalatal gate by the rear of the tongue. The front of the tongue raises up and the back lowers causing glossopalatal gate to open, the nasal aperture to close and the larynx to elevate. The food is propelled into the pharyngeal cavity and cleared with an anterior and posterior movement of the tongue. The soft palate and the posterior pharynx appose the tongue as the food enters the pharynx. The laryngeal aperture closes (protecting the lungs) as the epiglottis is pushed downward, and the upper esophageal sphincter opens allowing the food to pass into the esophagus. As the food clears the pharynx and passes down through the esophagus, the epiglottis re-opens the laryngeal aperture, and the tongue returns to its original shape opening the nasal cavity. The food passes on down through the esophagus to the stomach (through a second sphincter).

A particular swallowing exercise taught by the present invention is to have a patient cause a point about ¼-½ inch behind the tip of the tongue to touch the flex point of the palate on the roof of the mouth (the area where the palate starts to curve down to the incisal) with the mouth closed. The patient presses the tongue against the roof of the mouth from the ¼-½ inch point to a rear point so that about ⅓ of the tongue is pressed against the roof of the mouth. The patent now swallows without releasing the tongue. The rest of the tongue moves up, back, and then down to bring the food into the pharynx. After finishing the swallow, the patient continues to keep the ⅓ of the tongue touching the palate. This exercise causes throat volume to increase by proper placing of the mandible and maxillary relative to the head. This, in turn, causes the posture and strength to improve.

The exercise just described can be used in combination with one or more mouth guard appliances to correct retrude bite and other bites that are caused by improper muscle balance, or to simply improve posture. Various deformities of the face and jaw are due to a deviated swallow and muscle imbalance. The upper jaw can become displaced (narrow and down from the premolar-molar area, with the anterior area being pushed forward and sometimes tipped downward). This is a movement of the bones, and teeth. It is really a muscle problem that can be treated with an appliance and the swallowing exercise described. Using an appliance, the patient bites the anterior teeth together voluntarily in a slot provided in the appliance and moves the jaw if necessary. If the patient performs this bite exercise for a minimum of about an hour or more a day, considerable improvement can be realized.

Figure 1B:
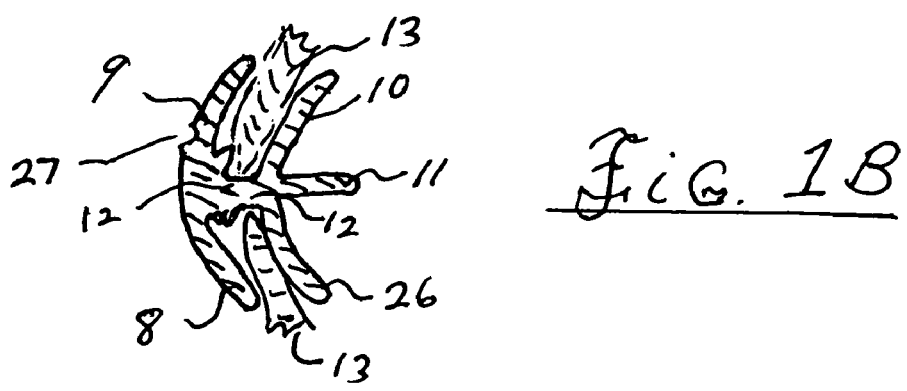

Turning to FIGS. 1A-1G and 2A-2D, a pre-fabricated appliance is shown. This can be pre-made with silicon or other similar materials and have a pre-made upper and lower trough that will cause the teeth to move into those positions, tip the upper jaw up and back, widen the upper jaw, retrain the jaw muscles, and reset the lower jaw to a new position. FIG. 1A shows the top and bottom jaw view of the device, while FIG. 1B is a cross section taken at the front of the mouth. The teeth shown are incisors 1, canine 2, pre-molars 3, and molars 4. The device 5 fits around the teeth and has an outer lip 25. The device is shaped to fit top and bottom with a special trough 6 (12 in FIG. 1B) located to receive the top and bottom teeth. The trough can run around from left to right around the front of the mouth. The trough normally starts at the upper right 3rd molar, then around the center of the mouth 7 and back to the upper left 3rd molar.

Figure 1C:
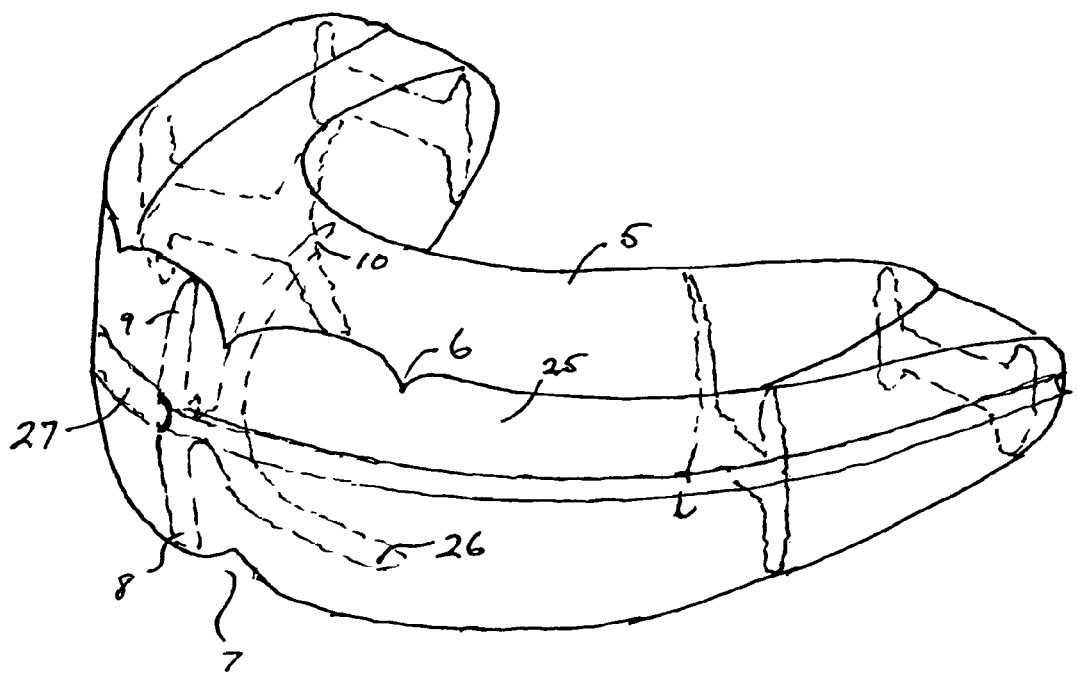
Figure 1D:
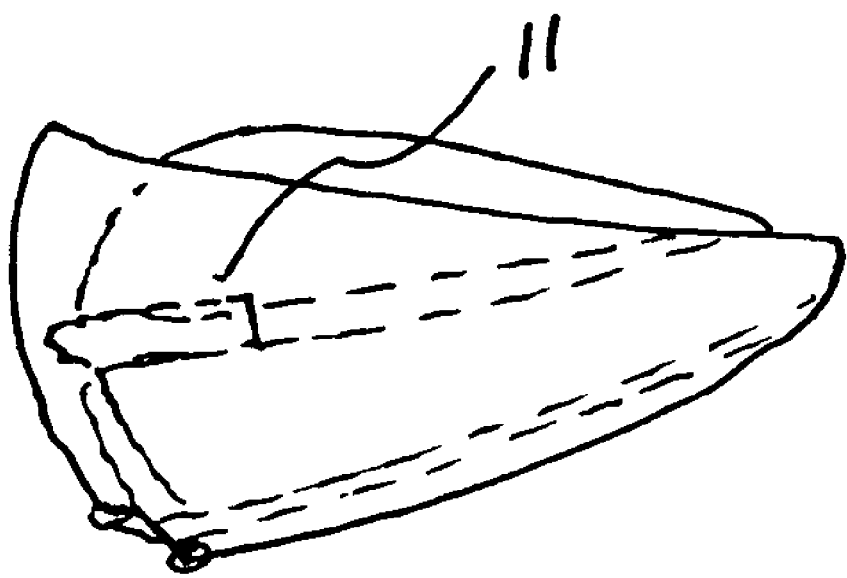

On the bottom, the trough runs from the lower right 3rd molar to the lower right 3rd molar. A tongue positioner 11 of around 20 mm can be placed at the center of the device, and can generally slant up around 5 degrees. The indentations 12, 6 can be sized to match the upper and lower teeth. Particularly in FIG. 1B, incisors 13 can be seen fitting into a section 12 of the device. The outermost separation of the trough from front 9 to back 10 on top is preferred to be around 7 mm. On bottom from front 8 to back 26 is preferred to be around 5 mm. An optional slot 27 can be provided for a 1.5 mm or similar hard wire. By biting the anterior teeth (which are the central lower incisor to the central upper incisor) to a predetermined separation, the appliance can guide the teeth and move the lower jaw to the preset trough. The upper canine will be lower by around ½ mm from the central and lateral incisors. The premolar to molar also pushed up. The lower canine has room to move above the central and lateral incisors by around ½ mm, and the premolar and molar have room to erupt higher. The upper teeth will be outside the lower teeth from the incisor to the molar with more offset on the molar. The appliance shown in FIG. 1 can be made from silicone or other similar material. Since this appliance is prefabricated, there can be cutting and sizing if required. FIG. 1C shows an embodiment of the appliance in a perspective view from the front, while FIG. 1D shows the appliance from the side. The tongue positioner 11 can slant upward from around 2.5 to around 5 degrees.

Figure 1E:
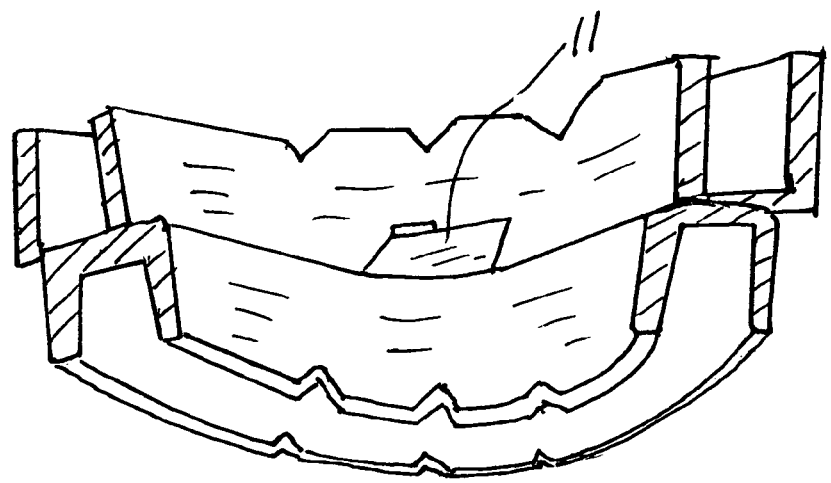
Figure 1F:
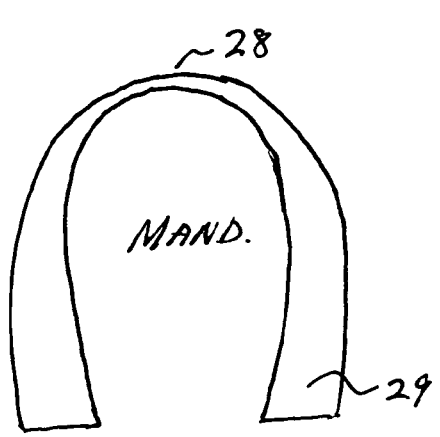
Figure 1G:
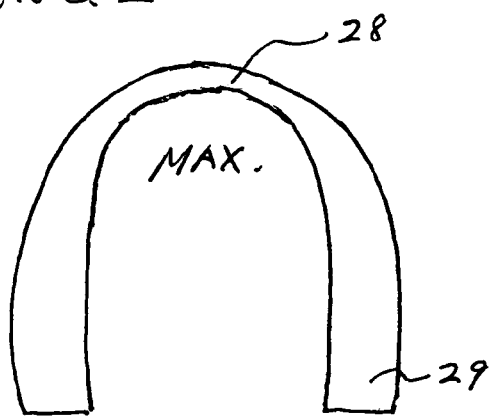

FIG. 1E shows a section of the device. FIGS. 1F and 1G show Mand. and Max. views of the device. The bite 29 receives the molars and the front 28, which has a trough or slot width of around 1 mm thick with a width and thickness of around 2-3 mm between the upper and lower central incisor, receives the incisors. FIG. 2A shows a facial view (looking from the front) of the upper part, while FIG. 2B shows palatal view (looking from the palate or rear). FIG. 2C shows a facial view of the lower part, while FIG. 2D shows a lingual view (looking from the tongue or rear). Each part has slightly different dimensions. The dimensions from notch to notch for the different parts are around 29 mm for the upper facial 30, about 22 mm for the upper palatal 31, about 25 mm for the lower facial 32 and about 21 for the lower lingual 33. The rear thicknesses are around 1-2 mm for the upper piece 34, 35 and around 1-2 mm for the lower pieces 36, 37. The total span (circumference) of the upper piece is around 80 mm, while the total span for the lower piece is around 73 mm. These distances are determined by taking the width of each tooth into account. The bite plane of the device is around 2-3 mm thick to receive the incisor then tapers down to around 1 mm at the end of $3^{rd}$ molar. The Max. buccal flange height is around 12 mm at the central incisor ($1^{st}$ notch) then tapers down to around 10 mm at the $2^{nd}$ notch and then tapers down to around 1 mm at the end of $3^{rd}$ molar. The Max. palatal flange is around 10 mm at the $1^{st}$ notch then tapers down to around 8 mm at the 2nd notch, and tapers down to around 1 mm at the end. The Mand. buccal flange height is around 10 mm at the $1^{st}$ notch, then tapers down to around 8 mm at the $2^{nd}$ notch, and tapers down to around 1 mm at the end. The lingual flange's height is around 10 mm at the $1^{st}$ notch, then tapers down to around 8 mm at the $2^{nd}$ notch, and tapers down to around 1 mm at the end The parts should be symmetric left to right, both top and bottom.

This appliance aligns the upper and lower jaw to an offset position with the lower jaw being exercised to bite forward and up for a deep and/or retrude lower jaw. The slant of the bite plane pushes the upper posterior bones and teeth upward leaving room for the lower teeth to move up when the patient moves the jaw so the front teeth bite together. By stretching the muscles and setting the jaw with the swallow bite, the patient can correct a deep or retrude bite (since it is muscles that cause these abnormal bites). A primary concept of the present invention is that it is possible to exercise facial muscles using the techniques and appliances herein described and illustrated. This can be done voluntarily during the day and maintained during the night using a combination of the swallowing technique taught along with one or more of the appliances. It should be noted that the appliances and the preferred dimensions given are for adults; however, it is possible to use the present invention with children as well. The swallowing technique is the same, but normally the appliances are made smaller to fit children's mouths. The appliances can also be made larger for a larger person.

As previously stated, the appliance of FIG. 1 can be preformed with a trough from the right 3rd molars to the left 3rd molars top and bottom. By biting the anterior teeth together, the appliance will guide the teeth (lower central incisor to upper central incisor) to the preset trough position. This causes the anterior bones to be pushed up and back. The upper canines will be around ½ mm lower than the central and lateral incisors. The premolars to molars' bones area will also be pushed up and out. The lower canine will have room to move above the central and lateral incisor by ½ mm, and the premolar to molar will have room to come up higher. The upper teeth will be outside the lower teeth from incisor to molar with more offset on the molar.

Another type of appliance is a mouth-guard used in various athletic activities such as football and wrestling. This type of appliance can be designed to set the lower jaw and swallow bite with or without athletic gear. The apparatus can be a type of mandibular orthopeadic reposition appliance (MORA) and can thus be part of an orthodontics treatment. The appliance, combined with orthodontics can permanently set the jaw to the swallow bite position described.

The pre-made hot water moldable mouth guard appliances of the present invention have a general outline as follows: the troughs are around 4 mm at the incisal and around 12 mm at the end of $3^{rd}$ molar, There is generally no offset on upper and lower bite plane (No offset on both upper buccal flange to lower buccal flange, and the same with the lingual flange).

The preferred method is to make mouth-guard appliances of the present invention from using pre-made, hot water thermoplastic molding or custom made. When a stock device is placed into hot water, it becomes softer and can be molded for a particular patient. This can be done directly in the mouth. The process is to have the patient perform the swallowing exercise while the practitioner adjusts the jaw opening from during steps 2-5 of the process to be described as they are repeated until there is no head or neck movement when the patient swallows. At this time, the doctor will mark two positions, the first from the nose and the second from the chin and measure the opening. Then the doctor places the mouth guard in hot water and goes through steps 2-5 with the predetermined measurement of the lower jaw position set.

The process for creating and sizing the mouth-guard appliances of FIGS. 3-6 is generally as follows:
1. The patient stands straight.
2. The patient opens the mouth wide, and the doctor places two fingers against the upper right and left canine teeth and squeezes
3. The doctor places two pieces of wax against the right and left either lower or upper premolar or molar teeth, and the doctor pushes the 2 upper central incisors or left and right canine with the thumb or any two fingers.
4. The patient bites down slowly through the wax.
5. Within 5 mm from the upper and lower incisors meeting, the patient performs the swallow exercise previously described. Some people who cannot perform the swallow exercise; then they will swallow as they normally do. There should be no head movement (only the Adam's apple moves).
6. Steps 2-5 are repeated with a slight adjustment of the lower jaw more open or more closed until there is no head or neck movement during the exercise swallow or normal swallow.
7. The doctor takes a bite registration for custom made mouth-guard or just marking at the nose and chin for pre-made mouth-guard to set the correct position of the upper and lower jaw.
8. The appliance can be fabricated from thermoplastics or other material.

As was stated, steps 2-5 are normally repeated until there is no head or neck movement during swallowing. The apparatus gives optimum throat volume during swallowing. Using it, the patient can not only improve the position of the jaws, balance the facial muscles, but also improve posture and increase strength.

An alternate method to achieve the first step is to have the patient stand straight with their eyes closed. They tilt their head down, and then think of a string that pulls the head up at the back. With breath out, they slightly tuck in their stomach, and then slowly tilt their head up until the patient feels that the eyes are horizontal. This is the correct position to perform the remaining steps.

FIGS. 3-4 show a lower (or upper) jaw mouth-guard appliance, while FIGS. 6A-6G show a full mouth mouth-guard. The appliance body 14 has an occlusal bite pad 15 with a sloping variable thickness of around 2 mm 18 at the 3rd molar 17 to around 5 mm 19 at the intersection of the first premolar and the canine 16. The notches shown in FIGS. 2-3 are used as guide lines in case there is a need to cut. The notches correlate with the 1st-2nd molars and the 2nd-3rd molars. If the device is used as a lower appliance, then the body 14 has a buccal flange. There is also a lingual flange. The flanges on the body 14 act like a wrap around the lower teeth and extend beyond the teeth to the gingivae on outside to protect the teeth, gingivae and bone from impact. The inside flange can be thinner. The preferred dimensions of the body thickness are around 2 mm thick for the buccal, 2 mm thick on the occlusal and around 1 mm thick on the lingual. The appliance shown in FIGS. 2-3 can also be made as an upper jaw guard appliance by reversing top to bottom.

Figure 3A:
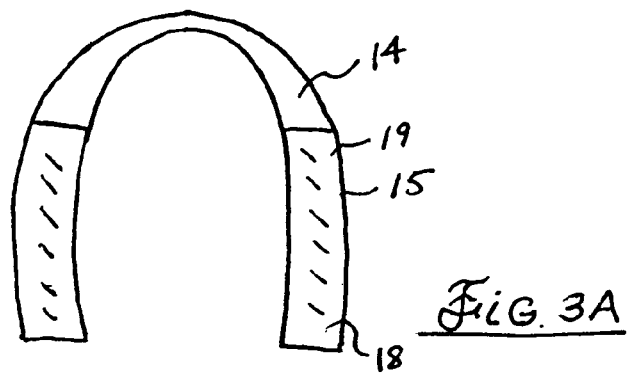
FIGS. 3A-3D show a lower or upper mouth-guard appliance.
Figure 3B:
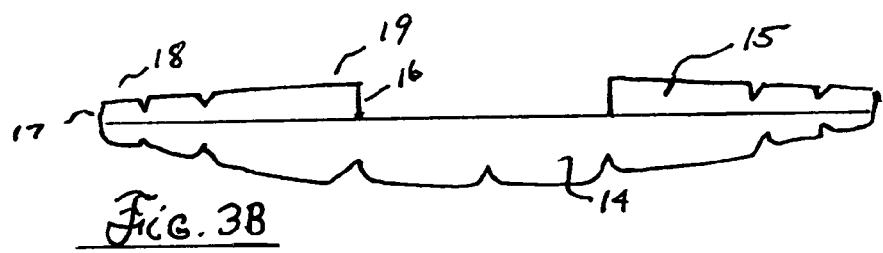
Figure 3D:
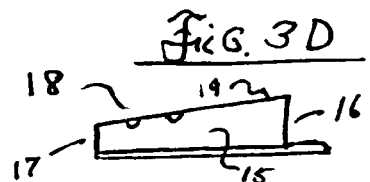
Figure 3C:
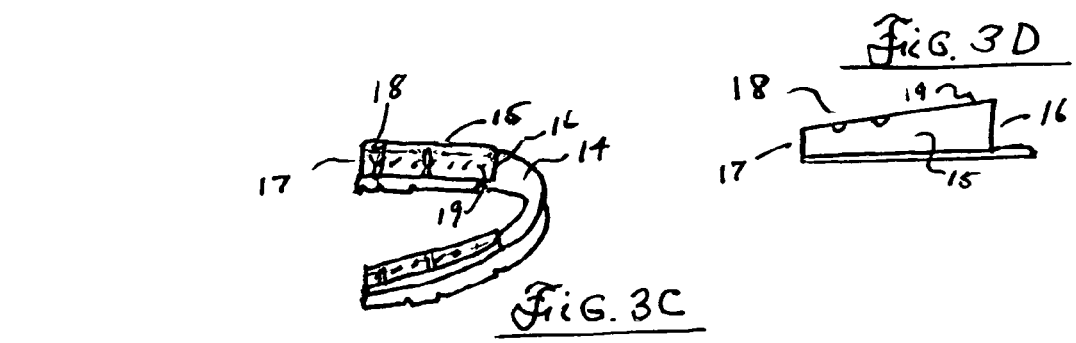
Figure 4A:
FIGS. 4A-4B show the lower jaw mouth-guard in a person's mouth and from the rear.
Figure 4B:
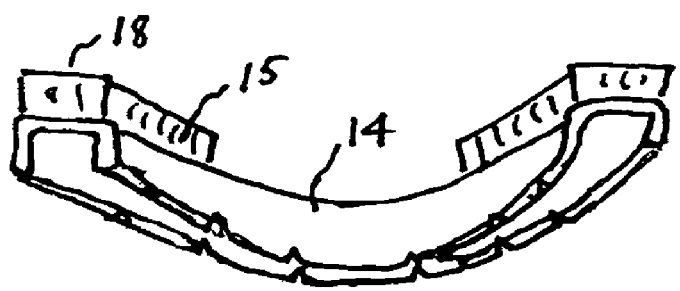

FIG. 3A shows a top view of the lower or upper appliance. FIG. 3B is a laid-flat front view to show the construction of the appliance. FIG. 3C is a perspective view, while FIG. 3D is a side view. FIG. 4A shows a lower mouth guard embodiment mounted in a patient's mouth. FIG. 4B is a back view from an angle slightly below level.

Figure 5A:
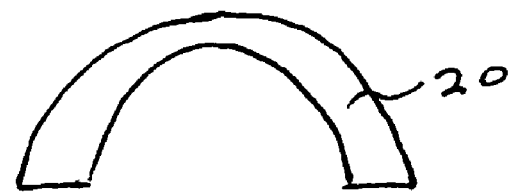
FIGS. 5A-5C show a night-guard appliance for use while a patient sleeps.
Figure 5B:
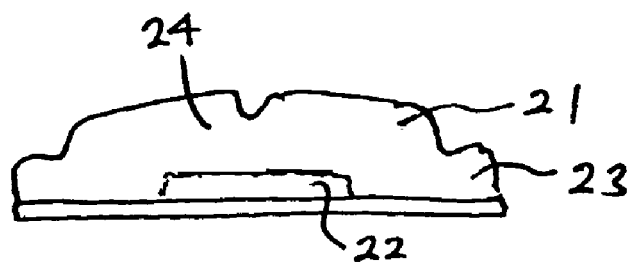
Figure 5C:

It is also possible to use the concepts of the present invention to design a night-guard appliance that is only worn by a patient in a prone position while sleeping. This is because during sleep, a human swallows automatically about once per minute and under stress a person will clench and grind. FIGS. 5A-5C show an embodiment of a night-guard device. A bite plate 20 can be seen in FIG. 4A which is a top view. The device normally extends only from canine to canine left and right; however, an alternate embodiment can extend from premolar to premolar. A buccal flange 21 can be seen in FIG. 5B which is a facial view. The height at the back 23 can be around 10 mm, while the height at the front 24 can be around 15 mm. FIG. 5C shows a lingual or back view. The bite plate 20 can extend back about 20 mm 22 in the front and tilts downward at around 15-30 degrees. The bite pad part of the device extends from canine to canine.

Figure 6A:
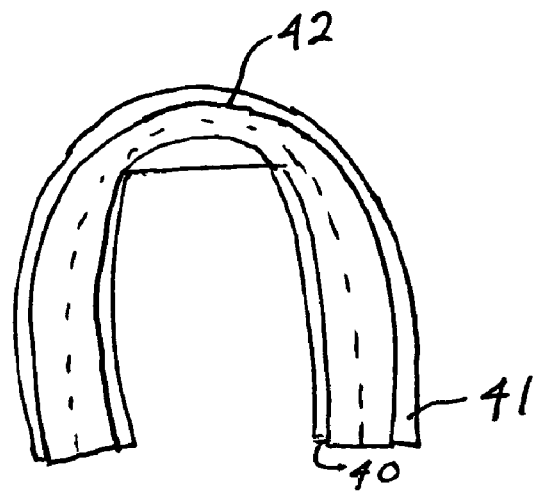
FIGS. 6A-6G show a full mouth mouth-guard appliance.

FIGS. 6A-6E show a full mouth guard appliance. FIG. 6A shows a symmetrical apparatus with a buccal and lingual flange. The palatal flange 40 can be around 1-2 mm, and the facial flange 41 can be around 2-3 mm. The bite block 42 can extend back around 16 mm from the facial flange, and can be around from 2 to 7 mm thick.

Figure 6C:
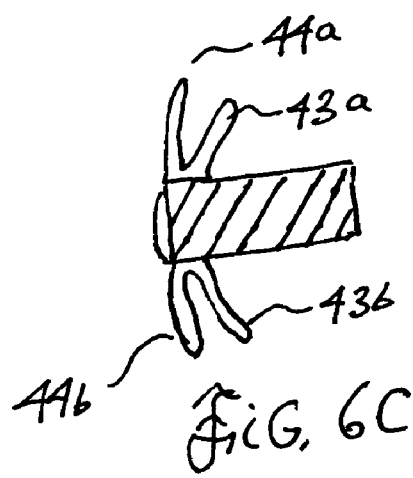
Figure 6B:
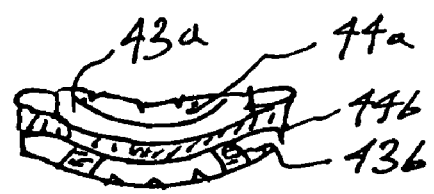

FIG. 6B shows an appliance from a lingual view with a bite pad of around 6 mm at the central incisal that tapers to around 2 mm at the end of the $3^{rd}$ molar. An upper and lower lingual flange 43a and 43b can be seen as well as an upper and lower facial flange 44a and 44b. The flanges on the upper part act to wrap around the upper teeth, and extend beyond the teeth to the gingivae on the outside to protect the upper teeth, gingivae and bone from impact. The flanges have a thickness of around 2-3 mm. The lower buccal flange is extended from the bite pad down on the outside to the $3^{rd}$ molar, and the lingual flange to between the $2^{nd}$ and $3^{rd}$ notch (the flange is only at the $1^{st}$ molar and $2^{nd}$ premolar). FIG. 6C is side view section showing the front bite block extending back 16 mm, with thickness 6 mm at the bite pad and extending at canine to canine. The facial flanges 44a and 44b and the lingual flanges 43a and 43b can be clearly seen.

Figure 6D:
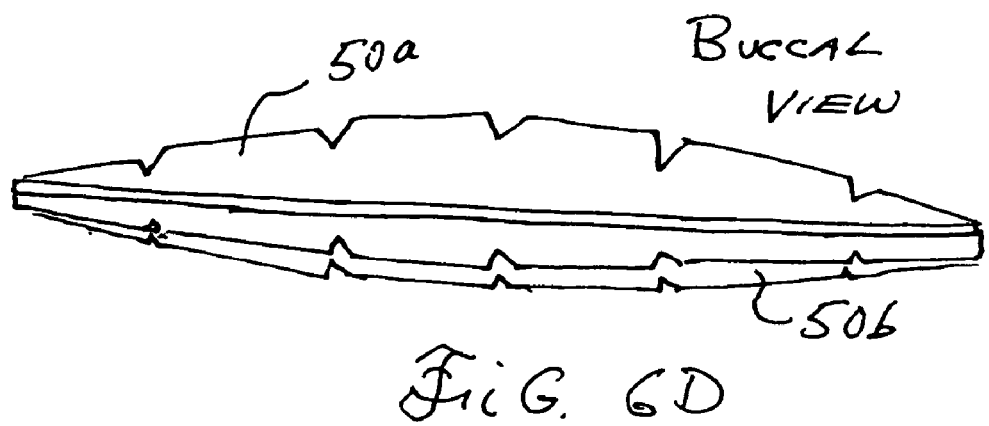
Figure 6E:
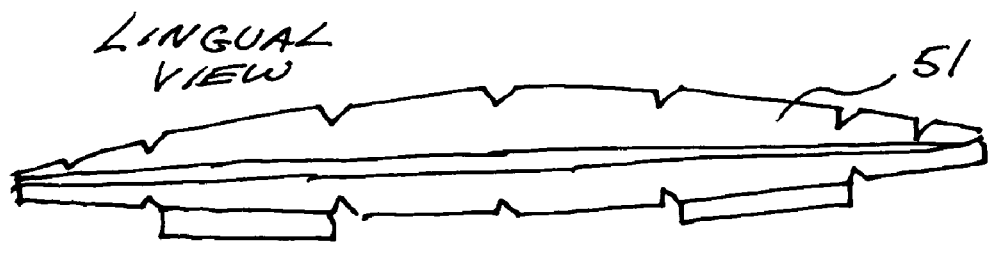

FIG. 6D shows appliance at the facial with the buccal flange 50a and 50b having height around 15 mm at the $1^{st}$ notch (central incisor) and tapering down to around 13 mm at the $2^{nd}$ notch and down to around 8 mm at the $3^{rd}$ notch and to around 1 mm at the end. The palatal flange 51 has a height of around 12 mm at the $1^{st}$ notch which tapers to around 10 mm at the $2^{nd}$ notch and then tapers down to around 4 mm at the $3^{rd}$ notch and around 1 mm at the end. Since the bite block is on the lower side (mandibular side), the buccal flange with reference to the bite block is around 6 mm lower at the $1^{st}$ notch, around 4 mm at the $2^{nd}$ notch and tapers down to the bite block around 0 mm at the end. The lingual flange is around 4 mm between the $2^{nd}$ and $3^{rd}$ notch.

Figure 6F:
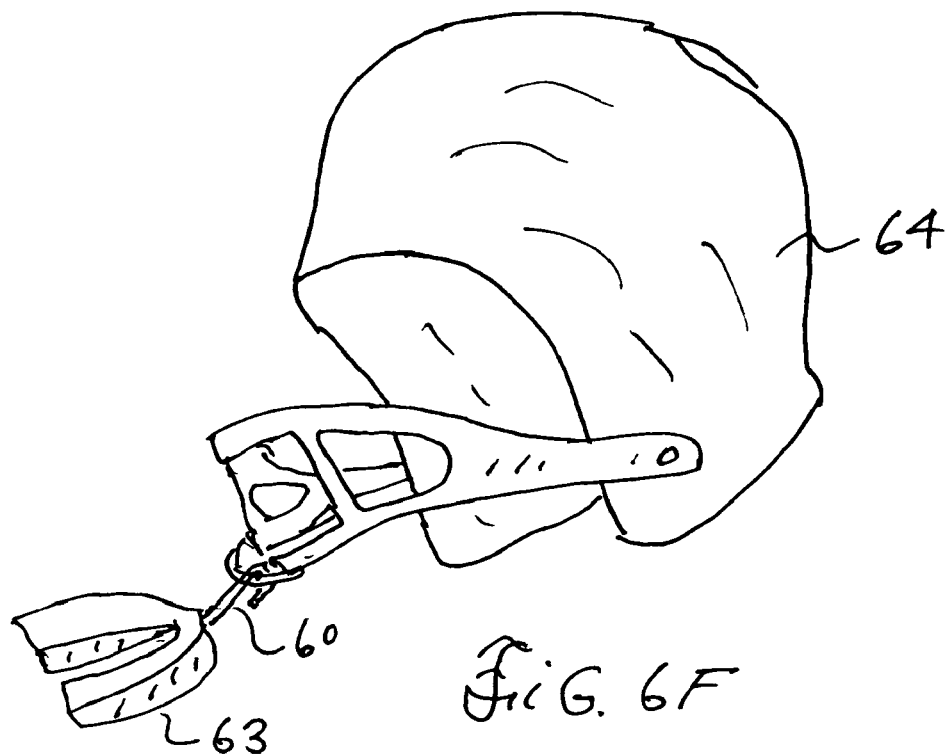
Figure 6G:
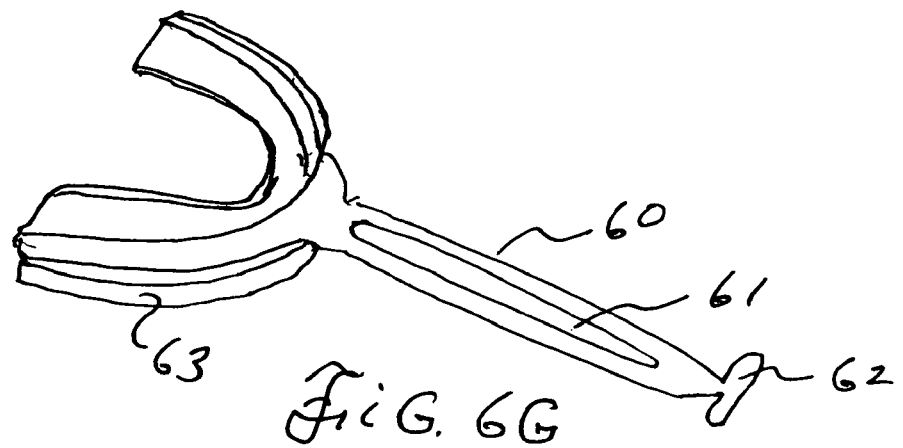

The full mouth-guard shown in FIGS. 6F-6G can have a strap 60 connecting to the front of the mouth piece 63 that is adjustably attached to the sports headgear 64. The strap can have a slit in the middle 61, and the end can include a cross bar 62.

Several descriptions and illustrations have been presented to aid in the understanding of the present invention. One skilled in the art will realize that numerous changes and variations can be made without departing from the spirit of the invention. Each of these changes and variations is within the scope of the present invention.

I claim:

1. A method for swallow control that results in increased jaw strength comprising:
   providing an oral apparatus adapted to be worn by a patient during a swallowing exercise, the oral apparatus having both a top trough and a bottom trough to receive said patient's teeth, the top trough extending front-wise from an upper left third molar to an upper right third molar, the bottom trough below said upper trough extending from a lower left third molar to a lower right third molar, said oral apparatus also including a tongue positioner of around 20 mm length at front center of said apparatus slanting upward around five degrees, wherein, with said oral apparatus in place, upper canine teeth are held lower by around ½ mm from central and lateral incisors, and lower canine teeth are held higher by around ½ mm from the central and lateral incisors;
   providing a swallowing exercise to said patient to be practiced while wearing said oral apparatus, the oral apparatus having both a top trough and a bottom trough to receive said patient's teeth, said oral apparatus also including a tongue positioner at front center of said apparatus slanting upward around five degrees, wherein the patient bites the oral apparatus and practices the swallowing exercise, the swallowing exercise having the steps of:
   pressing a point from around ¼ to around ½ inch rearward of the tip of the tongue to the flex point of the palate;
   holding around ⅓ of the tongue against the roof of the mouth;
   swallowing without releasing the tongue from the roof of the mouth;
   holding the tongue against the roof of the mouth after said swallowing.

\* \* \* \* \*